US011324453B2

(12) United States Patent
Matthiesen et al.

(10) Patent No.: US 11,324,453 B2
(45) Date of Patent: May 10, 2022

(54) SYSTEM FOR ADAPTIVE FILTERING OF CARDIAC SIGNALS

(71) Applicant: CathVision ApS, Copenhagen N (DK)

(72) Inventors: Mads Emil Matthiesen, Copenhagen K (DK); Sigge Nejst Larsen, Copenhagen N (DK)

(73) Assignee: CathVision ApS, Copenhagen N (DK)

( * ) Notice: Subject to any disclaimer, the term of this patent is extended or adjusted under 35 U.S.C. 154(b) by 16 days.

(21) Appl. No.: 16/341,812

(22) PCT Filed: Oct. 13, 2017

(86) PCT No.: PCT/EP2017/076208
§ 371 (c)(1),
(2) Date: Apr. 12, 2019

(87) PCT Pub. No.: WO2018/069509
PCT Pub. Date: Apr. 19, 2018

(65) Prior Publication Data
US 2019/0261927 A1    Aug. 29, 2019

(30) Foreign Application Priority Data
Oct. 13, 2016  (EP) .................................... 16193692

(51) Int. Cl.
*A61B 5/316*  (2021.01)
*A61B 5/00*   (2006.01)
(Continued)

(52) U.S. Cl.
CPC ............ *A61B 5/7203* (2013.01); *A61B 5/282* (2021.01); *A61B 5/316* (2021.01); *A61B 5/349* (2021.01);
(Continued)

(58) Field of Classification Search
None
See application file for complete search history.

(56) References Cited

U.S. PATENT DOCUMENTS

| 5,357,956 | A | 10/1994 | Nardella |
| 6,027,500 | A | 2/2000 | Buckles |

(Continued)

FOREIGN PATENT DOCUMENTS

| CA | 2359445 A1 | 4/2003 |
| EP | 2446814 A1 | 5/2012 |

(Continued)

OTHER PUBLICATIONS

International Search Report and Written Opinion of International Searching Authority for Application No. PCT/EP2017/076206, dated Dec. 12, 2017 (12 pages).

(Continued)

*Primary Examiner* — Michael W Kahelin
*Assistant Examiner* — Michael A Rizzuto
(74) *Attorney, Agent, or Firm* — Nixon Peabody LLP (57) ABSTRACT

System for filtering cardiac signals. The system includes: cardiac terminals (10a-d) adapted to collect cardiac electrophysiological potentials from a plurality of cardiac electrodes (1a-d) placed at respective cardiac locations in or on an individual (99) and a processor device (40) adapted to process one or more input signals, which are based on the collected electrophysiological potential(s). The processing includes running an adaptive filter algorithm on one or more signals based on the input signals. The adaptive filter algorithm is arranged to calculate estimated noise component(s) of the signals and arranged to subtract the estimated noise component(s) from the signals. In this way a cardiac signal is derived where the noise has been significantly reduced.

20 Claims, 7 Drawing Sheets

(51) Int. Cl.
  *A61B 5/282* (2021.01)
  *A61B 5/349* (2021.01)
  *A61B 5/30* (2021.01)
  *A61B 5/287* (2021.01)

(52) U.S. Cl.
  CPC ............ *A61B 5/725* (2013.01); *A61B 5/7221* (2013.01); *A61B 5/7257* (2013.01); *A61B 5/287* (2021.01); *A61B 5/30* (2021.01); *A61B 5/6823* (2013.01); *A61B 5/6852* (2013.01)

(56) References Cited

U.S. PATENT DOCUMENTS

| | | |
|---|---|---|
| 8,248,137 B2 | 8/2012 | Peuscher |
| 9,579,060 B1* | 2/2017 | Lisy .................... A42B 3/0453 |
| 2003/0036685 A1* | 2/2003 | Goodman .............. A61B 5/021 |
| | | 600/300 |
| 2005/0113703 A1* | 5/2005 | Farringdon .......... A61B 5/0205 |
| | | 600/509 |
| 2005/0119708 A1 | 6/2005 | Haefner |
| 2006/0293603 A1 | 12/2006 | Strandberg |
| 2007/0225610 A1* | 9/2007 | Mickley ................. A61B 5/287 |
| | | 600/509 |
| 2009/0177097 A1* | 7/2009 | Ma ..................... A61B 5/14551 |
| | | 600/500 |
| 2011/0190625 A1 | 8/2011 | Harlev |
| 2011/0227638 A1 | 9/2011 | Peuscher |
| 2012/0109242 A1 | 5/2012 | Levin et al. |
| 2013/0184600 A1 | 7/2013 | Tan |
| 2014/0121548 A1* | 5/2014 | Lou ........................ A61B 5/725 |
| | | 600/509 |
| 2014/0364715 A1 | 12/2014 | Hauck |
| 2015/0005585 A1 | 1/2015 | Xu |
| 2016/0166171 A1 | 6/2016 | Warner |
| 2016/0242700 A1* | 8/2016 | Ferber .................. A61B 5/7278 |
| 2016/0248434 A1 | 8/2016 | Govari |
| 2017/0156606 A1* | 6/2017 | Ferber ................ A61B 5/14539 |
| 2017/0224244 A1 | 8/2017 | Kuwabara et al. |
| 2019/0282180 A1* | 9/2019 | Babaeizadeh ........ A61B 5/7221 |

FOREIGN PATENT DOCUMENTS

| | | |
|---|---|---|
| EP | 2740403 A1 | 6/2014 |
| JP | H11-332842 A | 12/1999 |
| JP | 2011-072725 A | 4/2011 |
| JP | 2012-090986 A | 5/2012 |
| JP | 2016-524480 A | 8/2016 |
| JP | 2016152624 A | 8/2016 |
| WO | WO 2010/103542 A2 | 9/2010 |
| WO | 2016024495 A1 | 2/2016 |

OTHER PUBLICATIONS

International Search Report and Written Opinion of International Searching Authority for Application No. PCT/EP2016/057783, dated Jun. 17, 2016 (10 pages).

Stevenson, W. et al.; "Recording Techniques for Clinical Electrophysiology"; Journal of Cardiovascular Electrophysiology, vol. 16, No. 9, pp. 1017-1022; Sep. 1, 2005; XP055222320; ISSN: 1045-3873.

International Search Report and Written Opinion of International Searching Authority for Application No. PCT/EP2017/076208, dated Dec. 13, 2017 (11 pages).

Razzaq, N. et al.; "An Intelligent Adaptive Filter for Elimination of Power Line Interference From High Resolution Electrocardiogram"; IEEE Access, vol. 4, pp. 1676-1688; Mar. 31, 2016; XP011611726.

Yegui, X. et al.; "A new LMS-based Fourier analyzer in the presence of frequency mismatch and applications"; IEEE Transactions on Circuits and Systems Part I: Regular Papers, vol. 52, No. 1, Jan. 10, 2005; XP055355532.

U.S. Appl. No. 16/341,717, filed Apr. 12, 2019, Mads Emil Matthiesen, Filtering Device for Recording Electrophysiological Signals.

English translation of Notice of Reasons for Refusal, with search report, in Japanese Patent Application No. 2019-519981, dated Jul. 14, 2021 (18 pages).

English translation of Notice of Reasons for Refusal, with search report, in Japanese Patent Application No. 2019-520019, dated Jul. 26, 2021 (19 pages).

* cited by examiner

SYSTEM FOR ADAPTIVE FILTERING OF CARDIAC SIGNALS

CROSS-REFERENCE TO RELATED APPLICATIONS

This application is a U.S. National Stage of International Application No. PCT/EP2017/076208, filed Oct. 13, 2017, which claims the benefit of European Patent Application No. 16193692.7, filed Oct. 13, 2016, both of which are incorporated herein by reference in their entireties.

The present invention relates in one aspect to a system for filtering cardiac signals, and in particular to a system for filtering cardiac signals representing electrophysiological potentials from a plurality of electrodes at respective cardiac locations. In particular the present invention relates to a system for filtering cardiac signals, the system comprising: a plurality of cardiac terminals adapted to collect cardiac electrophysiological potentials from a plurality of cardiac electrodes placed at respective cardiac locations in or on an individual and a processor device adapted to process one or more input signals which are based on the collected electrophysiological potentials.

It should be noted that according to this specification the term cardiac signals should be understood to refer to signals which relate in some form to electrophysiological potentials related to the function of an individual's heart. These signals could be intracardiac, i.e. measured inside the body or inside the heart, or measured externally to the body, i.e. via electrodes placed on the skin of the individual.

BACKGROUND OF THE INVENTION

Cardiac electrophysiological measurements are considered an important tool for understanding and treating cardiac problems, for example arrhythmia phenomena. Cardiac measurements can be taken inside the body/inside the heart (intracardiac) or outside the body. In the following, the discussion will focus mainly on intracardiac measurements, but the invention as defined by the claims, could also be used for cardiac measurements taken outside the body.

Intracardiac measurements are obtained in so-called minimally invasive procedures using intracardiac catheters. Advanced equipment includes multiple electrode catheters having a plurality of electrodes that can be located inside the heart. Depending on the procedures to be performed, such catheters are at their distal end equipped with electrodes configured for picking up an electrophysiological potential at the respective location of the electrodes. The electrophysiological potentials are passed via electrical conductors from the distal end of the catheter to a connector interface at the proximal end of the catheter, and further to recording equipment for amplification, processing, display and storage of signals representative of the intracardiac electrophysiological potentials. The intracardiac electrophysiological signals are the observation of the intracardiac electrophysiological potentials as a function of time, wherein the intracardiac electrophysiological signals are measured by amplifying the potential difference between a first terminal and a second terminal, wherein at least the first terminal is connected to an electrode that is placed inside the heart. The obtained intracardiac signals may be further amplified/processed and/or digitized for display on a computer and/or storage on a digital storage medium.

By recording/mapping a plurality of electrophysiological signals from signal electrodes placed inside the heart, details about a pathological state relating to cardiac arrhythmia in an individual can be obtained and proper treatment, such as an ablation treatment, can be developed. The aspects of the recorded intracardiac signals to be studied include the presence or absence of characteristic features in a given signal, the periodicity and regularity of repetition of the signals, as well as the amplitude and morphology of the signals.

Cardiac signals can also be measured by external electrodes placed on the surface of the body. Signals measured by external electrodes can also be used to study details about the cardiac behaviour of an individual as will be known to the person skilled in the art.

Two typical configurations for measuring cardiac electrophysiological signals are known—a unipolar configuration and a bipolar configuration. In the unipolar configuration, the cardiac signal is recorded by referencing the electrophysiological potentials from the cardiac signal electrode to a so-called indifferent electrode, which is considered to provide a potential reference that is largely independent of the local potential measured by the cardiac signal electrode. The indifferent electrode is typically arranged outside and distant from the heart. Commonly, the indifferent reference is obtained from one or more electrodes arranged on the outside surface of the individual, such as a Wilson central terminal (WCT) defined by connecting electrodes arranged on the arms and the left leg of a patient through high impedance resistors. However, previous studies also suggest using an intravascular electrode as reference electrode in order to reduce pick-up of mains interference. Such an intravascular electrode is, for example, advantageously arranged in the inferior vena cava (Stevenson et al., Journal of Cardiovascular Electrophysiology, 2005, pp. 1017-1022). Advantages of unipolar recordings include providing an increased spatial resolution of the local potentials at the signal electrode and providing information about the direction of impulse propagation. Disadvantages of unipolar recordings include a strong susceptibility to mains interference, and a tendency to retain far-field components that make it difficult to separate local from distant activity in the recorded signal. In the bipolar configuration the cardiac signal is recorded as the difference between two neighbouring cardiac electrodes. Thereby, far-field components of the recorded signal are largely eliminated, leaving only the local components of the electrophysiological signal. Advantages of the bipolar configuration include a low susceptibility to noise interference, and a more precise capture of high-frequency components. Disadvantages of the bipolar configuration include that the direction of propagation of activation with respect to the orientation of the electrode pair affects the amplitude of the recorded signal. The bipolar signal therefore does not provide reliable information on the direction of propagation of an activation wave front. Furthermore, the spatial resolution of the bipolar configuration is limited by the spatial separation between the two intracardiac electrodes used.

A major challenge in the recording of cardiac electrophysiological signals is the interference from electrical noise sources, which is picked up by the highly sensitive apparatus. Amongst the main causes for such noise is in particular the prominent mains interference at around 50 Hz or around 60 Hz—depending on the local frequency standard for mains supply. Other sources of noise include internal amplifier noise, artefacts due to movement of the wiring used for recording, and electrode DC-offsets. The noise may include noise components common to all signals (common mode noise) and noise components that vary from signal to signal (differential mode noise).

Processing the signals e.g. by filtering at frequencies corresponding to the noise sources may suppress some of the noise. However such filtering tends to affect the morphology of the signals and therefore has to be done with the utmost care. For example, a traditional method of reducing mains interference is to introduce a notch filter which blocks the mains frequency. For example, a notch filter could be used that blocks 50 Hz noise. However this has several issues. Cardiac electrograms contain 50 Hz components themselves, so a notch filter will both remove noise and relevant signal. Since the mains frequency always varies a bit around 50 Hz, a broader notch is needed and more relevant signal is lost. Another issue is that a notch filter will often create ringing artifacts after sharp signals.

US 2015/0005585 A1 discloses a system and method for the acquisition of bio-potential signals, such as, for example, ECG (electrocardiography), EEG (electroencephalography), or EMG (electromyography) signals. The disclosed bio-potential acquisition system uses multiple active electrodes attached to the outside of the body, in which each of the electrodes is integrated with an amplifier and an analogue-to-digital converter for the suppression of interference picked up from cables. An improvement of the bio-potential acquisition system according to US 2015/0005585 A1, resides in adjusting the gain of the amplifiers to compensate for component mismatch by feeding back a common mode test signal to an adjustable gain control of the amplifiers in the respective active electrodes. The system of US 2015/0005585 A1 relies on the use of active electrodes, in which pre-amplifying electronics is located next to and integrated with a passive electrode. However, in other applications, passive electrodes could be used where the measured signal is first amplified at a location distant to the electrode. Depending on the specific application, the person skilled in the art will be able to choose between passive or active electrodes.

Another prior art document which seeks to reduce common mode effects and signal noise is U.S. Pat. No. 8,248,137. In this document, the average of the output of the amplifier stage is fed back to the input of the amplifier stage. Different embodiments are disclosed, some using a Digital signal processor and some using analog means.

Applicant's own patent specification PCT/EP2016/057783, filed on the 8 Apr. 2016 is incorporated by reference herein in its entirety. The techniques disclosed in this specification can also be used to reduce common mode effects and to reduce signal noise.

A disadvantage of cardiac electrophysiological signals obtained from known set-ups is that a user of the signals is confronted with data that can still be noisy or deprived of valuable information content that may be useful, or even indispensable, in the context of a particular study, analysis, diagnosis or treatment for which the data is to be used.

It is therefore desirable to provide a technique for obtaining cardiac electrophysiological signals that allows for an even more efficient suppression of noise; that is easily re-configurable depending on context; that overcomes at least some of the above-mentioned limitations; and/or that provides an alternative to known systems.

It should be noted that the systems disclosed in the current patent specification can be used in combination with the systems disclosed in the above mentioned prior art patent specifications or on their own.

SUMMARY OF THE INVENTION

The above mentioned objectives are solved at least in part in that said processing comprises running an adaptive filter algorithm on one or more intermediate signals which are based on the input signals to the processor, said adaptive filter algorithm being arranged to calculate one or more estimated noise component(s) of said one or more intermediate signals and being arranged to subtract said one or more estimated noise component(s) respectively from said one or more intermediate signals.

In this way, noise, especially noise due to mains interference, can be effectively removed from a cardiac signal without causing large distortions of the actual signal.

In one embodiment, the signals are measured by intracardiac electrodes placed inside the body and/or inside the heart. In another embodiment, the signals are measured by external electrodes placed on the body of the individual. In certain embodiments, passive electrodes are used while in other embodiments, active electrodes with built in amplification are used.

It should be noted that in typical signal processing applications in medical applications, combinations of analog and digital signal processors are used. For example it is typical to use an analog amplification stage followed by a digital signal processing stage. The adaptive filter algorithm of the current invention will run in the digital processor. However the signal from the electrodes can be processed in many ways prior to being input to the adaptive filter algorithm. Hence the language of the claims which discusses potentials at the electrodes which are converted to input signals to the processor. The adaptive filter algorithm is then based on intermediate signals which are based on the input signals to the processor. It should be noted that while amplification is typically performed analog, it could also be performed at least partially digitally. Likewise, the adaptation algorithm according to the current invention can be placed at different places in the signal flow. In the examples presented below, the adaptive filtering is placed as the last step in the signal processing, but it could also be placed earlier on in the signal flow if desired.

In one embodiment, the one or more estimated noise components of said adaptive filter algorithm could be estimated as one or more sinusoidal waves where the amplitude, the phase shift and the frequency are estimated by the adaptive filter algorithm. Since mains interference typically takes the form of a sine wave, estimating the noise as a sine wave, in many cases, gives a very good result. In one embodiment the one or more estimated noise components could be assumed to be in the form $n=a \sin(\theta)+b \cos(\theta)$.

In one embodiment the adaptive filter algorithm could be based on a non-linear filter algorithm. Two non-limiting examples of such a non-linear filter algorithm are an extended Kalman filter and an unscented Kalman filter. The person skilled in the art of non-linear filters will be able to choose additional relevant filters.

In a more specific embodiment, the system further could comprise one or more indifferent terminal(s) adapted to collect one or more indifferent electrophysiological potentials from one or more indifferent electrodes placed in or on the individual and in that the processor could also be arranged to process one or more indifferent input signal(s) based on the one or more collected indifferent electrophysiological potential(s). The use of an indifferent signal in the processing of the signals provides a good way of maintaining the proper morphology of the signals. In one embodiment, the adaptive filter algorithm could include signals based on said one or more indifferent input signal(s). In one specific embodiment, the indifferent terminal(s) could be adapted to collect indifferent electrophysiological potentials from one or more indifferent electrodes probing an intracardiovascular location in the individual.

In another specific embodiment, the system could further comprise an amplifier stage which is a differential amplifier stage adapted to amplify the electrophysiological potentials collected from the cardiac and/or indifferent terminals with respect to a signal reference to obtain respective cardiac and/or indifferent signals and wherein the signal reference is based on an average of the obtained respective cardiac and/or indifferent signals and where the input signals to the processor are based on the cardiac and/or indifferent signals.

In one embodiment the processor device could further be adapted to determine respective unipolar cardiac signals by subtracting one or more of the one or more indifferent signals from the cardiac signals and in that the adaptive filter algorithm is run on one or more signals based on said unipolar cardiac signals. In this way, the correct morphology of the signals can be ensured.

In one embodiment of the digital filter algorithm, the processor could be adapted to calculate an average of more than one of the one or more cardiac signal(s) and/or the one or more indifferent signal(s) and in that said calculated average is used by the adaptive filter algorithm to provide a first estimate of the frequency of the noise components. Since the mains interference should be the same for many of the signals, using the average of multiple signals should provide a good estimation of the frequency of the mains interference.

In one embodiment of the filter algorithm, the signal or signals to be filtered could be filtered by one or more band pass filter(s) on the one or more cardiac signal(s), said band pass filter(s) being centred around the expected mains frequency and/or the expected harmonics of the mains frequency. In this way, the noise due to the mains interference can be essentially isolated so that it is easier to make an estimation of the mains interference noise.

Since a band pass filter introduces a phase shift to the signal, the system could compensate the one or more estimated noise component(s) prior to subtracting it (them) from the input signal with the known phase shift of the band pass filter.

Since the mains interference can occur at the mains frequency and at different harmonics of the mains frequency, the processor could be adapted to analyse the frequency spectrum of one or more of the one or more cardiac signals to determine the frequency or the frequencies which contribute(s) the most to the noise. The adaptive filter algorithm could then be run multiple times, starting with the frequency which has the greatest contribution to the noise, and repeated at relevant harmonics, the estimated sine waves of each frequency being summed prior to being subtracted from the input signal. In this way, noise due to harmonics can also be captured. In this case, band pass filters could be used as described above centred around the frequency of interest.

In another embodiment, the adaptive filter algorithm could also be run multiple times, starting with the frequency which has the greatest contribution to the noise, and repeated at relevant harmonics. However, instead of running all the estimates for each frequency on the same signal and then summing the contributions, in this embodiment, an estimate of the sine wave for the largest contributing frequency is run first, and then this estimated noise is subtracted from the input signal, after which the process is repeated for the next frequency on the newly created signal.

In one embodiment, the frequency analysis could be performed via a Goertzel algorithm at the expected mains frequency and at relevant harmonics of the expected mains frequency. In this way, it is possible to find the contribution to the overall noise of the different frequencies. By using a Goertzel algorithm, the computational load can be reduced since it is already known at which frequencies it is most likely to find mains interference noise.

Since it is known that the system could experience spikes in the measurement signals which are due to external influences, the process could include a spike detection algorithm and the processor could be arranged to pause the adaptation of the noise estimation for a specific amount of time when a spike is detected in the cardiac signal. In one embodiment the specific amount of time is related to the impulse response of the band pass filter. In this way, the spikes will not contribute to distorting and corrupting the estimation of the noise signal.

In a further aspect, the invention relates to a method for processing cardiac signals, in particular a method for processing cardiac signals representing electrophysiological potentials probed by a plurality of electrodes at respective cardiac locations based on the systems described above. In yet a further aspect, the present invention could be combined with other systems for performing intracardiac procedures such as applying stimulus and/or ablation energy at intracardiac locations.

BRIEF DESCRIPTION OF THE DRAWINGS

Preferred embodiments of the invention will be described in more detail in connection with the appended drawings, which show in FIG. 1 Schematic of a set-up including a system for filtering cardiac signals according to one embodiment of the invention.

DETAILED DESCRIPTION OF PREFERRED EMBODIMENTS

Figure 1:
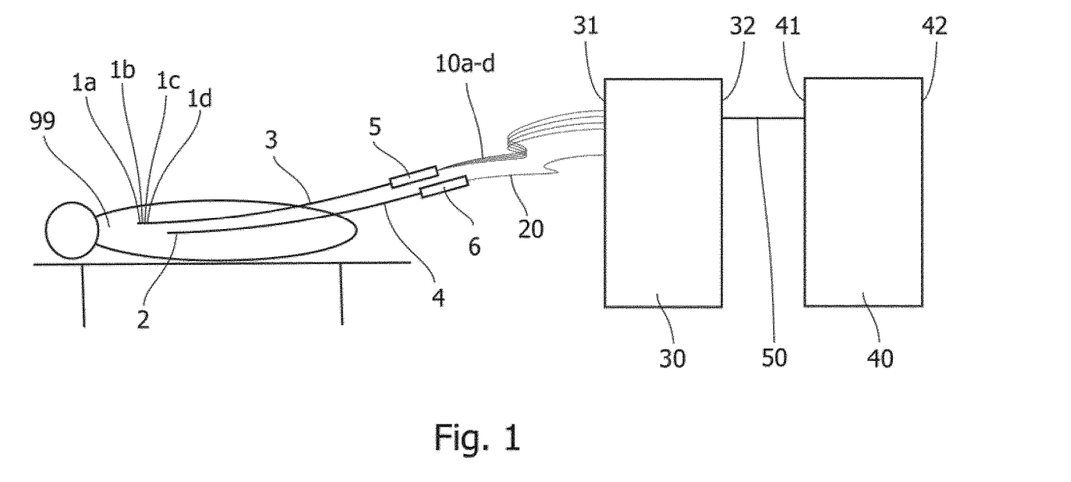

FIG. 1 schematically shows a set-up for recording intracardiac signals from an individual 99 using a system according to one embodiment of the invention. In this embodiment, the system comprises a plurality of intracardiac terminals 10*a-d* that are connected to respective intracardiac electrodes 1*a-d* at the distal end of a multi-electrode catheter 3 via an interface 5 at the proximal end of the catheter 3. The system further comprises an indifferent terminal 20 that is connected to an intra-cardiovascular indifferent electrode 2 at the distal end of a catheter 4 via an interface 6 at the proximal end of the catheter 4. A typical set-up may include further apparatus, such as for 3D mapping catheter probes, for monitoring the individual, for stimulation of the heart, for applying defibrillation, and/or for performing ablation procedures. Such further apparatus has been omitted in FIG. 1 for reasons of clarity. The system further comprises a differential amplifier stage 30 and a processor device 40 communicating with each other via a link 50.

Prior to recording, the electrodes 1a-d have been placed in an intracardiac location in a known manner, e.g. in a minimally invasive procedure by means of a catheter 3 carrying the plurality of electrodes 1a-d. The intracardiac electrodes are located within the same heart chamber to be monitored and probe the intracardiac electrophysiological potentials at their respective intracardiac locations. Accordingly, the indifferent electrode 2 has been placed in an intra-cardiovascular location, e.g. in the inferior vena cava, by means of a catheter 4, and probes electrophysiological potentials that are considered indifferent with respect to the intracardiac electrophysiological potentials. Alternatively, the indifferent electrode may be placed on the surface of the body using a surface electrode.

The probed electrophysiological potentials from the electrodes 1a-d, 2 are transmitted to the interfaces 5, 6 at the proximal end of the catheters 3, 4 via respective leads. Advantageously, the intracardiac electrodes 1a-d and their respective leads are bundled in a single catheter 3, whereas the indifferent electrode 2 is placed on a separate catheter 4. However, different bundling combinations may be conceived, e.g. a set-up where the intracardiac electrodes 1a-d and the indifferent electrode 2 are grouped on one catheter, or a set-up comprising multiple catheters comprising multiple groups of intracardiac electrodes for simultaneously probing intracardiac potentials at respective locations. Furthermore, the number of four intracardiac electrodes shown in FIG. 1 is to be considered as an example and different numbers of intracardiac electrodes, such as 5, 6, 7, 8, 9, 10, 20, 50, 100, or even more may be conceived.

The intracardiac potentials from the intracardiac electrodes 1a-d are collected at interface 5 by the respective intracardiac terminals 10a-d. Accordingly, the indifferent potential from the indifferent electrode 2 is collected at interface 6 by the indifferent terminal 20. While the indifferent potential provided at the interface 6 in the set-up shown in FIG. 1 is defined by a single electrode 2, it may also be conceived that the indifferent potential collected by the indifferent terminal 20 is defined as a combination of potentials probed by a plurality of electrodes.

The intracardiac and indifferent electrophysiological potentials collected by the terminals 10a-d, 20 are passed on the input side 31 of the differential amplifier stage 30 to respective amplifier channels where they are amplified with respect to a signal reference. The respective intracardiac and indifferent signals obtained from the amplifier stage 30 are passed from an output side 32, via link 50, to an input interface 41 of a processor device 40. Details of the processing are presented later on in this specification. Furthermore, the reader is referred to applicants co-pending patent application PCT/EP2016/057783 for even more details.

Figure 2:
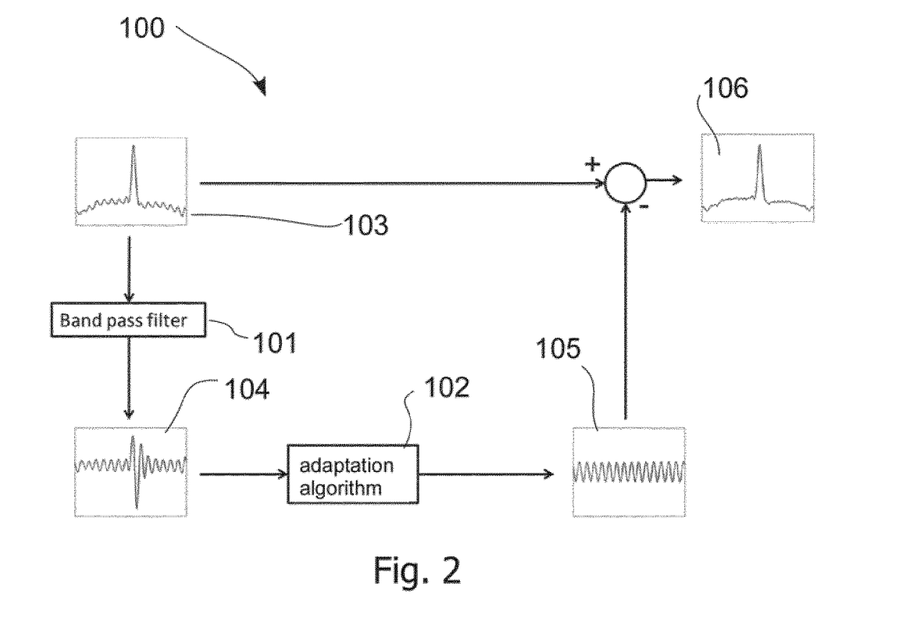
FIG. 2 Schematic flow chart showing function of adaptive filter.

FIG. 2 shows a schematic and simplified overview of one embodiment of the filtering method used by the system according to the current invention. The main elements of the adaptive filter 100 are a bandpass filter 101 and an adaptation algorithm 102. The bandpass filter is centred around a certain frequency, typically the mains frequency, e.g. 50 Hz, and is used to isolate the noise signal from the input signal 103. Since the partially isolated noise signal 104 also contains part of the physiological signal, the adaptation process 102 uses the partially isolated noise signal 104 to generate an estimation of the noise signal as a pure sine wave 105. The sine wave amplitude, phase shift and frequency are continuously estimated based on the bandpass filter output, and finally the estimated sine wave is subtracted from the original input signal 103 to generate an output signal 106 which has a reduced amount of noise.

In certain embodiments of the system, the system could make use of additional elements to further improve the filtering effect. One additional element is compensation for the band pass filter. The bandpass filter causes a small phase shift, which causes the synthesized noise signal to not match the actual noise signal completely. This phase shift can be corrected in the sine wave synthetization. Another additional element is to compensate for the noise signal at different harmonics of the mains interference. For example, often 150 Hz noise and other harmonics are also present along with 50 Hz noise when the mains frequency is 50 Hz. The algorithm can be run several times to get rid of those also. In one embodiment, if the 150 Hz noise is higher than the 50 Hz noise, the algorithm could be run for 150 Hz first. A detection algorithm can be introduced to decide which frequency should be filtered first. A further additional element could be to compensate for peaks or spikes in the signals. Sharp and high peaks in the signal can disturb the adaptation process. A spike detection algorithm can be introduced to set the adaption on pause, when a high peak has occurred.

In one embodiment of the adaptation algorithm, an extended Kalman filter can be used. It is to be noted that Kalman filters and extended Kalman filters are known in the art and as such the entire details of the implementation of an extended Kalman filter will not be repeated here. In the current embodiment five parameters are estimated and continuously updated. The noise signal at sample k is estimated as $$n_k = a_k \cos(\theta_k) + b_k \sin(\theta_k) \quad (1)$$

The five parameters are the instantaneous phase $\theta_k$, the instantaneous frequency $f_k$, the central frequency $f^0_k$, and two amplitude parameters $a_k$ and $b_k$. The update of each parameter is modelled to set up the state space model $$X_{k+1} = \Phi X_k + \Gamma U_k \quad (2)$$

$$y_k = h_k(X_k) + v_k \quad (3)$$

where $X_k$ is the parameter vector, $\Phi$ is the state transition matrix, h is the nonlinear measurement function (see Eq. 1), $U_k$ is process noise and $v_k$ is measurement noise. In this context, measurement noise is anything that is not part of the sine wave, so both random noise and physiologic potentials. Process noise expresses how much and how fast each parameter can change, e.g. how much the frequency deviates from 50 Hz. For each new sample of the raw signal, the parameters are updated taking into account both the expected development of each parameter and the actual value of the new sample.

In order to make the adaptation algorithm more robust, a spike detection function can be introduced in some embodiments. A large spike, for instance from cardiac stimulation, will disturb the adaptation algorithm because the initial bandpass filter will cause ringing artefacts. When a spike is detected, the adaptation mechanism is set to pause for 60 ms, which is the settling time for this specific bandpass filter. In one specific embodiment of the adaptation algorithm, the algorithm goes as follows:

1. Initialization:
   a. Values for the five parameters and for their covariances are initialized based on intelligent assumptions. For example the frequency can be initially estimated to 50 Hz in Europe, even though it is known that the actual frequency deviates from 50 Hz.
   b. A bandpass filter is initialized around the mains frequency, e.g. 50 Hz and the group delay for the bandpass filter is found and saved for later.
2. Pre-processing:
   a. A spike detection measure is computed based on the amplitude and first difference of the signal.
   b. The raw signal is bandpass filtered with the filter initialized in step 1.b above.
3. For each sample in the bandpass filtered signal:
   a. The parameters are first updated as in Eq. 2, where only the model is considered.
   b. A weighting parameter called Kalman gain is computed (method not shown here).
   c. If there has been a spike within the last 60 ms, the parameters are not further updated.
   d. If there have been no spikes, the updated parameters are adjusted to also take the current measurement sample into account. The contributions from the model and from the measurement respectively are weighted with the Kalman gain.
   e. The noise sample is computed with Eq. 1, but with the phase adjusted to compensate for the delay caused by the bandpass filter.

It should be noted that this algorithm can also be implemented for real-time processing, where initialization is only done once, and where pre-processing and noise estimation is done continuously or in small segments, when new input signals are received from the amplifier.

Figure 3:
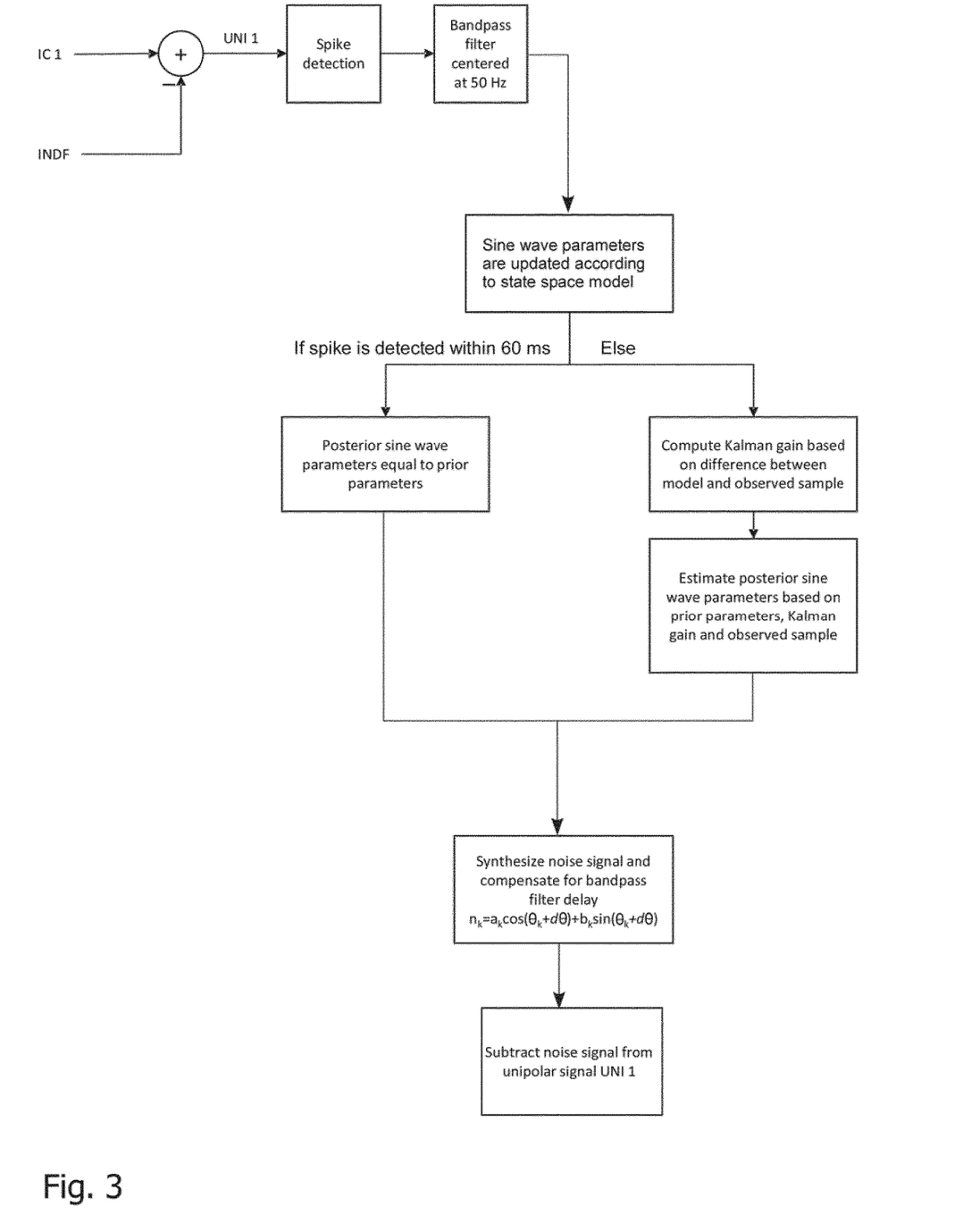
FIG. 3 Flow chart showing a first embodiment of an adaptive filter according to the invention.

The algorithm is illustrated in more detail in FIG. 3. In this figure, the amplified indifferent signal INDF is first subtracted from the amplified signal IC1 to form a unipolar signal UNI 1 representing the measurement provided by the first intracardiac electrode. This signal is fed to a spike detection algorithm which detects large fluctuations in signal. The signal is not affected by the spike detection algorithm, but the output of the spike detection algorithm determines the flow of the algorithm later on in the process.

The signal is then band pass filtered at a frequency around the mains frequency. The band pass filter is adjusted to ensure that the expected deviations in the mains frequency are captured. This should essentially isolate the noise due to the mains interference. The sine wave parameters are then calculated based on the state space model and the prior parameters.

If a spike has been detected in the spike detection algorithm, then the adaptation algorithm is skipped. However, if there has been no spike in the last 60 ms, then the adaptation algorithm continues. The first step is to calculate the Kalman gain based on the difference between the model and the observed sample. Then posterior sine wave parameters are estimated based on the prior parameters, the Kalman gain and the observed sample.

Based on the newly estimated parameters, the noise signal is synthesized and compensated for the known phase shift of the bandpass filter. The synthesized noise signal is then subtracted from the unipolar signal UNI 1.

In general, it can be noted that the noise from mains interference is typically significant at the mains frequency, but it could also be significant at higher frequencies due to the harmonics of the mains frequency. If the noise contribution due to the higher harmonic frequencies is significant, then the algorithm could be used for both the mains frequency and for higher harmonics. If the noise at higher harmonics, e.g. 150 Hz, is higher than for 50 Hz, then it would be desirable to run the algorithm for 150 Hz first. The relative level of noise from the different harmonics can be estimated by an FFT or more efficiently by the Goertzel algorithm, which computes the DFT for only a specific set of frequencies. Use of the Goertzel algorithm is especially relevant when filtering for mains interference since it is known around which frequencies the noise will be expected. So an additional element in the algorithm is to first determine the most appropriate order of frequencies to filter. The Goertzel output can additionally be used to determine which harmonics need to be filtered, and which are of so low amplitude that they are negligible. This can for example be done in windows of 1 s.

Figure 4:
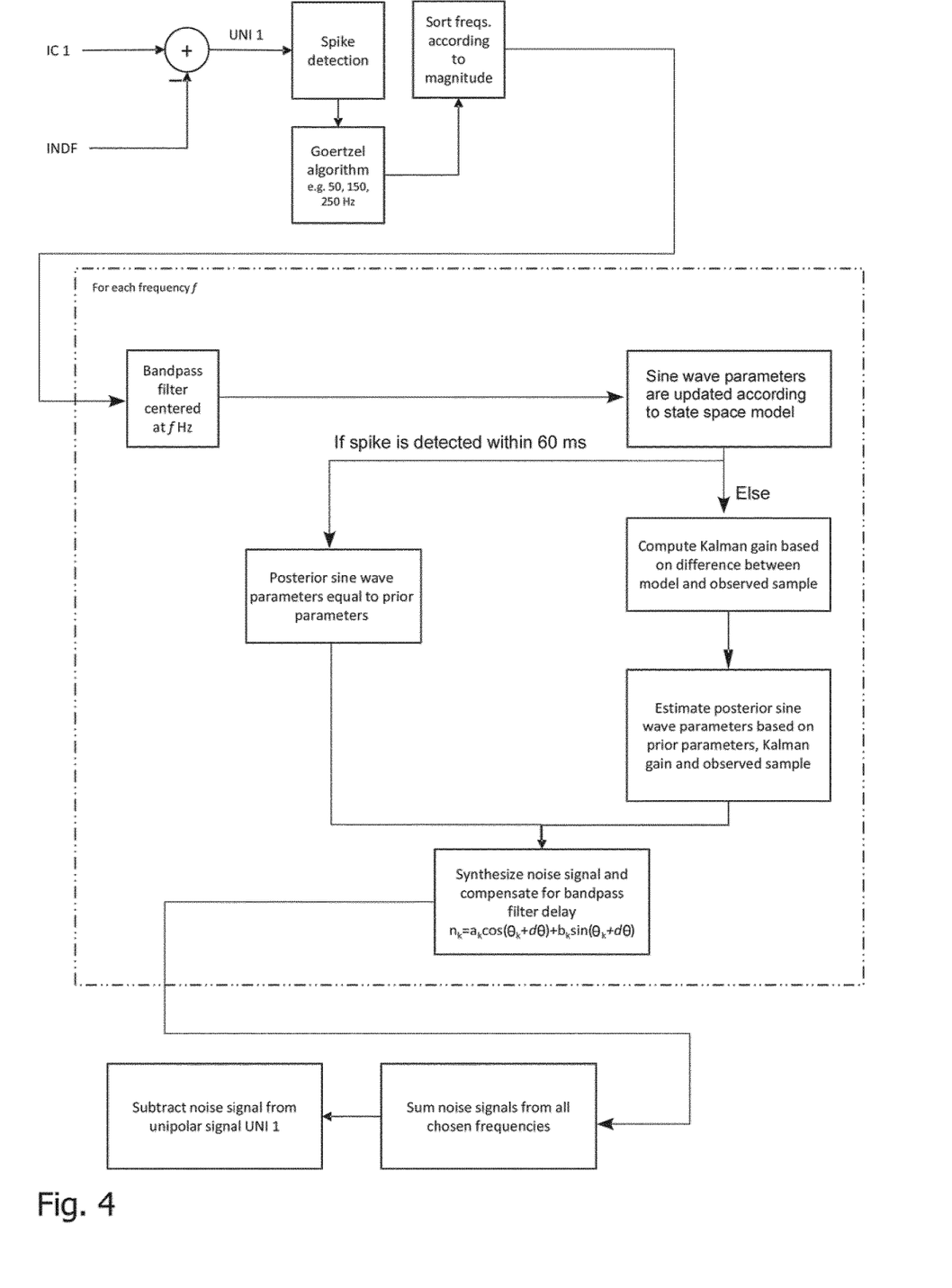
FIG. 4 Flow chart of a second embodiment of an adaptive filter according to the invention.

When the adaptation algorithm is run at multiple frequencies, then the contributions to the noise of the different frequencies can be handled differently. In one embodiment, the algorithm is run at each frequency but with the same input signal. The synthesized noise signals at each frequency are therefore estimated independently of each other and summed together at the end. The summation of the different synthesized noise signals is then subtracted from the Unipolar signal UNI 1. This is illustrated in FIG. 4. In another embodiment, instead of running the adaptations at the different frequencies independently of each other, the adaptations at the different frequencies can be run sequentially with the estimated noise signals being subtracted from the input signal prior to running the adaptation algorithm for the next frequency. For example, if the Goertzel algorithm determines that three frequencies contribute to significant noise, 50 Hz, 150 Hz and 250 Hz, then the algorithm of FIG. 3 could first be run for the frequency of 50 Hz. The synthesized noise signal for 50 Hz is then subtracted from the input signal UNI 1 to get a filtered version of UNI 1. The algorithm is then repeated for the frequency 150 Hz. But instead of using the original input signal UNI 1, in this case, the filtered UNI 1 signal is used as the input to the adaptation algorithm. At the end of the adaptation algorithm for 150 Hz, the noise signal is subtracted from the UNI 1 signal which has already been filtered with the noise signal for 50 Hz. Finally the algorithm can be repeated for the case of 250 Hz noise.

Figure 5:
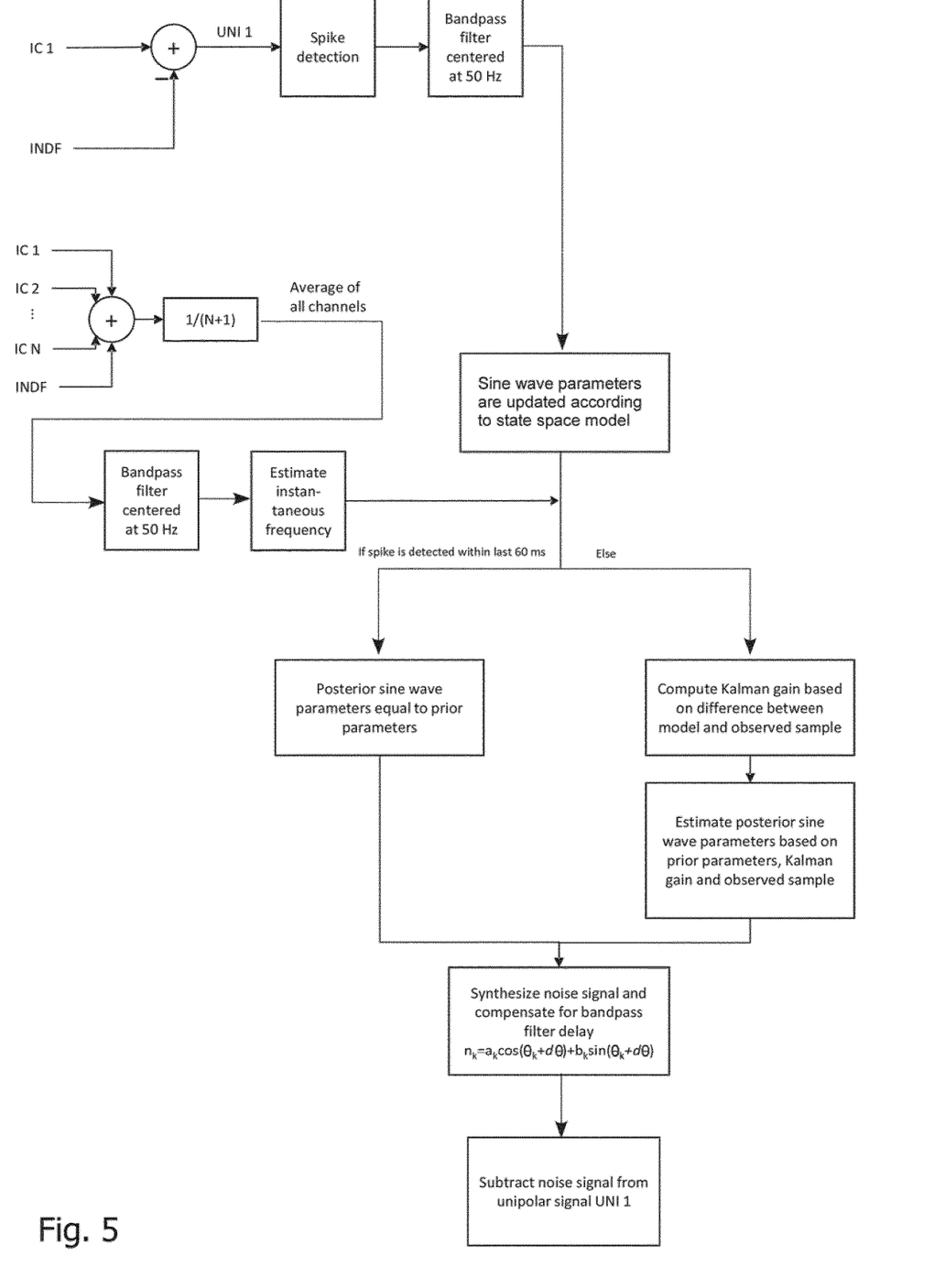
FIG. 5 Flow chart of a third embodiment of an adaptive filter according to the invention.

In most actual situations, there will be multiple signals which need to be filtered. Each of the signals will need to run their own adaptation algorithm which estimate the parameters of the noise model. However, it can be assumed that the frequency of the mains interference of all the signals will be essentially the same. Hence, in one embodiment, the average of all signals is computed to generate an estimate of the common-mode signal. Especially in the case where one or more indifferent electrodes are placed outside the heart, the estimated common-mode signal will almost entirely consist of mains noise and higher harmonics. That can be exploited, because the instantaneous frequency of this common-mode signal will be the same as in each individual signal, which means that this parameter can be estimated from a signal without any physiologic potentials. When there are no physiologic potentials, the estimation will be more robust and it will be faster to track changes in the frequency. This is illustrated in FIG. 5. It should be noted that the embodiment of FIG. 5 only calculates the noise at one frequency, however, it would also be clear that the concept of using the average of multiple signals to estimate the frequency and to run the algorithm multiple times at different frequencies could be combined.

Figure 6:
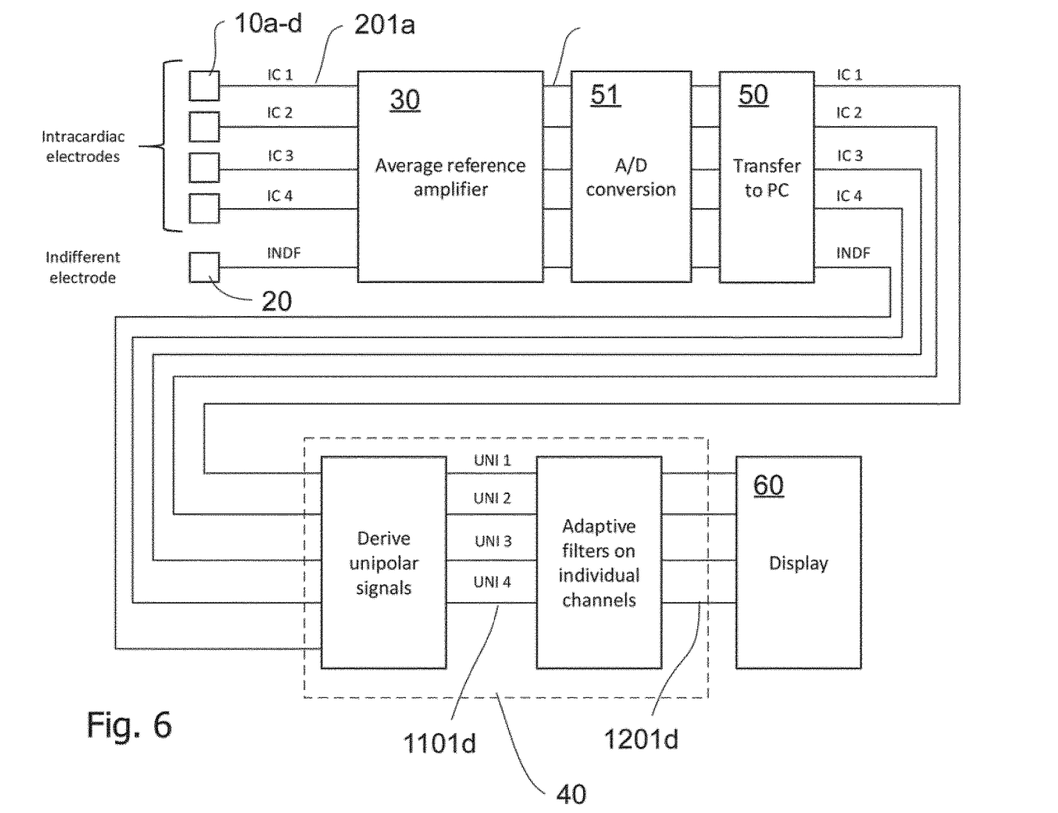
FIG. 6 Flow chart of a complete signal processing system comprising a filtering step according to the current invention.

Prior to using the adaptive filter as described above, the measured signals are amplified and in some cases unipolar signals are generated. FIG. 6 shows one embodiment of a complete system for signal processing. On the left side of the figure, the raw signals from the electrodes are connected to the input stage 31 of the amplifier via terminals 10a-10d,20. In this embodiment, the amplifier stage has an average reference amplifier configuration, wherein the average of all amplifier output signals is fed back to the input side of the amplifier stage and is used as the signal reference. Thereby a good first level suppression of mains interference as common mode noise is achieved already in the differential amplifier stage. In this embodiment, the differential signals are amplified by 20 and the common mode signal is amplified by 1. In this way, the CM signal is reduced by a factor of 20, but it is still a part of the signal. Alternatively, the amplifier stage has a common reference amplifier configuration, wherein an indifferent potential may be used as common reference for all amplifier channels.

In the embodiment shown in FIG. 6, the output of the average reference amplifier stage 30 is then transferred to a digital signal processor 40 via a link 50 which comprises an analogue to digital converter 51. In this embodiment, in order to generate unipolar signals, the amplified indifferent signal is subtracted from the amplified intracardiac signals. In this way, the Common Mode (CM) signal will be essentially removed from the intracardiac signals since the Common Mode signal is present in both the intracardiac signals and the indifferent signal. Typically, the noise in the signal will also be present in the CM signal and this subtraction step will also remove most of the noise. However, if some of the common mode signal is converted to differential signal prior to or during amplification, there will still be some 50 Hz noise in the signals. This 50 Hz noise will further be removed by the digital adaptive filters as described in more detail above. Finally the signals are displayed on a display 60 and/or recorded in a storage device (not shown).

In the following, the advantageous processing of intracardiac signals by the embodiment of FIG. 6 is described by way of example. Processing has been performed on different sets of signals that have been obtained on a pig 99 with a set-up corresponding to the one shown in FIG. 1, using a system 10, 20, 30, 40, 50 according to one embodiment of the system according to the invention.

Figure 7:
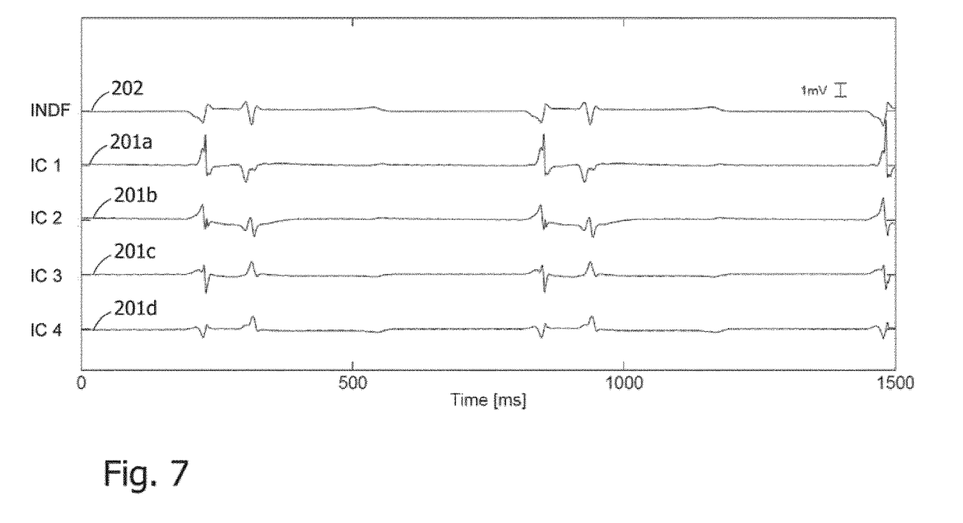
FIG. 7 Composite plot of a first set of signals including four intracardiac and one indifferent signal.

A first set of four intracardiac signals 201a-d (Channels 1-4) and one indifferent signal 202 (Channel IVC) is shown in the composite plot of FIG. 7, wherein all channels are shown on the same time scale and at the same vertical scale indicated by the vertical scale bar labelled 1 mV. The same time scale and vertical voltage scale also apply to the plots of FIGS. 8-10.

The intracardiac and indifferent signals 201a-d, 202 shown in FIG. 7 have been obtained by amplifying intracardiac and indifferent potentials collected from the intracardiac and indifferent terminals 10a-d, 20 in an average reference amplifier configuration using the arithmetic mean of all five channels as the signal reference fed back to the input side 31 of the differential amplifier stage 30.

Figure 8:
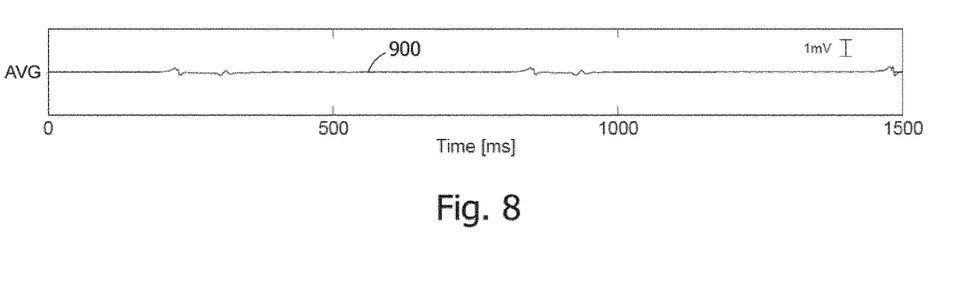
FIG. 8 Plot of the average of the signals of the first set.

FIG. 8 shows the arithmetic mean signal of all five signals of FIG. 7. It can be noted that the average signal is a good estimate of the common mode signal. As the number of signals increases, the average signal will more and more closely represent the common mode signal.

Figure 9:
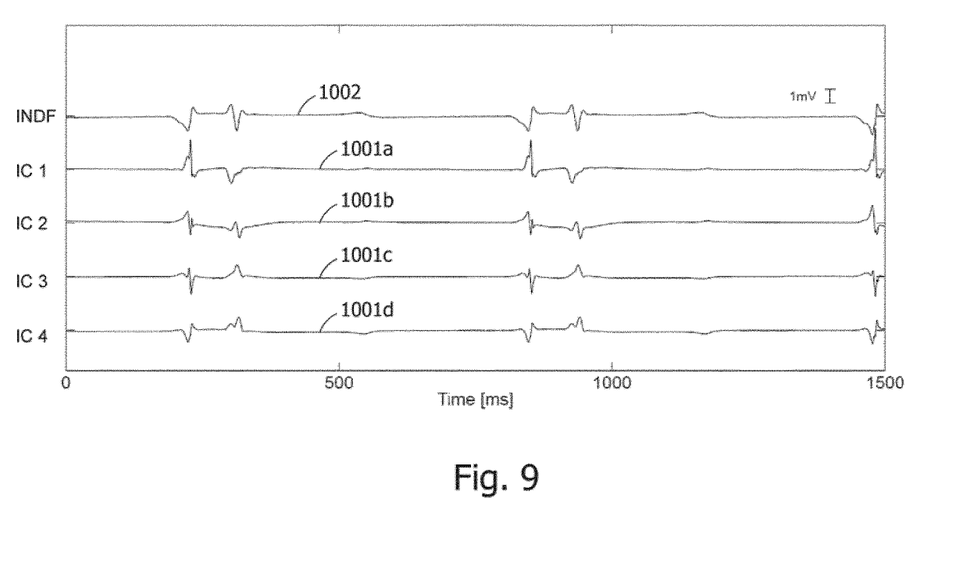
FIG. 9 Composite plot of differential mode intracardiac and indifferent signals obtained from the first set.

The estimated common mode signal 900 of FIG. 8 is then subtracted from each of the intracardiac and indifferent signals 201a-d, 202 of FIG. 7 to obtain the corresponding differential mode signals 1001a-d, 1002 shown in the composite plot of FIG. 9. The differential mode intracardiac signals 1001a-d may again be output as intracardiac data for further use. The differential mode signals 1001a-d exhibit again very little mains interference. Yet the morphology of the differential mode signals 1001a-d is distorted compared to the typical interpretation of unipolar signals. However, since the set of signals includes a compatible indifferent signal, the morphology may be restored by either directly subtracting the indifferent signal 202 from the intracardiac signals 201a-d to generate respective unipolar intracardiac output signals (not shown), or by subtracting the differential mode indifferent signal 1002 from the differential mode intracardiac signals 1001a-d to generate respective unipolar intracardiac output signals 1101a-d as shown in FIG. 10.

The short-cut of directly subtracting the indifferent signal from the intracardiac signals is possible without compromising the noise suppression properties of the method, when the signals are referenced to a common mode signal already in the amplifier stage, e.g. in the above-mentioned average reference amplifier configuration, which is also applied for the first set of signals 201a-d, 202. Including the steps of deriving the differential mode signals first before performing the subtraction is also possible in this case where the intracardiac signals are referenced to the common mode signal already in the amplifier stage.

As discussed previously, further improvements of the noise reduction may be achieved by selectively applying a channel-specific filtering step to one or more of the intracardiac and indifferent signals. As discussed above, using an adaptive digital filter is particularly advantageous in this case.

Figure 10:
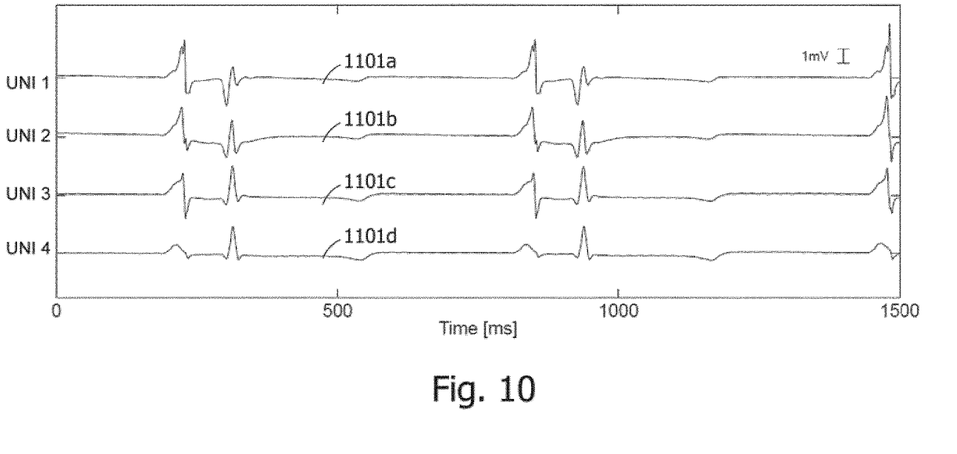
FIG. 10 Composite plot of intracardiac data with unipolar intracardiac output signals generated from the differential mode signals of the first set.
Figure 11:
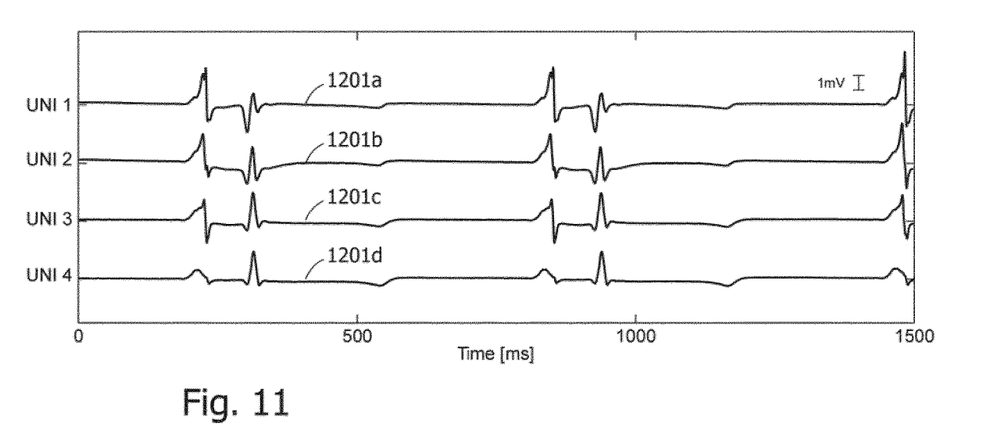
FIG. 11 Composite plot of filtered intracardiac data.
Figure 12:
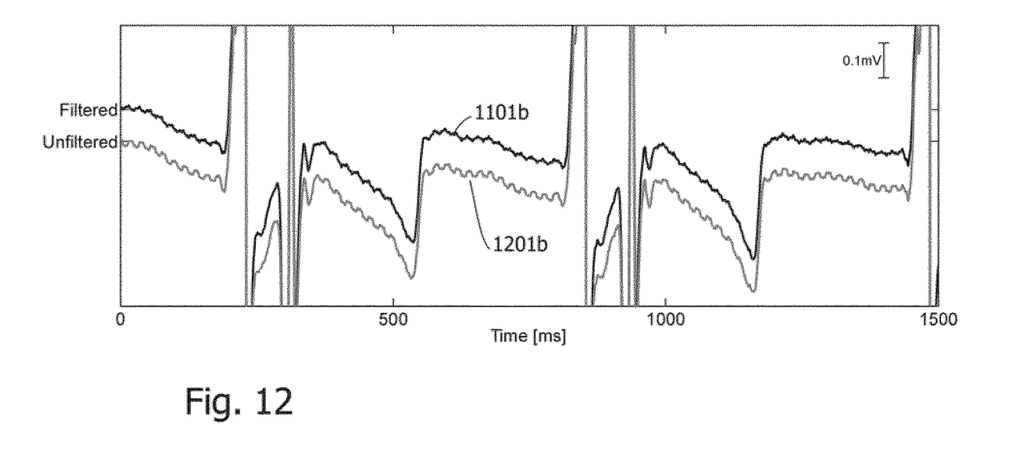
FIG. 12 Composite plot showing a zoomed in view of the filtered version and unfiltered version of the signals of FIG. 11.

FIG. 11 shows the resulting signals 1201a-d after the signals 1101a-d of FIG. 10 have been digitally filtered by an adaptive filter. FIG. 12 shows a zoomed in portion of a portion of one of the filtered signals 1201b of FIG. 11 and one of the unfiltered signals 1101b of FIG. 11.

It should be noted that the above description has presented some different embodiments with specific features. It should be clear to the person skilled in the art based on this disclosure, that the different specific features of the different embodiments could be combined in different manners.

The invention claimed is:

1. System for filtering cardiac signals, the system comprising:
   a plurality of cardiac terminals adapted to collect cardiac electrophysiological potentials from a plurality of cardiac electrodes placed at respective cardiac locations in or on an individual;
   one or more indifferent terminal(s) adapted to collect one or more indifferent electrophysiological potentials from one or more indifferent electrodes placed in or on the individual;
   an amplifier stage adapted to amplify the electro-physiological potentials collected from the cardiac and indifferent terminals with respect to a signal reference to obtain respective cardiac and indifferent signals; and
   a processor device adapted to process a plurality of input signals, wherein a first of the plurality of input signals is based on a cardiac signal and a second of the plurality of input signals is based on an indifferent signal, wherein said processing comprises running an adaptive filter algorithm on one or more intermediate signals based on the plurality of input signals, said adaptive filter algorithm being arranged to calculate one or more estimated noise component(s) of said one or more intermediate signals and being arranged to subtract said one or more estimated noise component(s) respectively from said one or more intermediate signals to generate a filtered output signal, wherein the processor device is adapted to calculate an average of more than one of the plurality of input signals including the indifferent signal as well as the cardiac signals, and wherein said calculated average is used by the adaptive filter algorithm to provide a first estimate of the frequency of the noise component with reduced common mode effects and reduced signal noise relative to the electro-physiological potentials.

2. System according to claim 1, wherein the one or more estimated noise components of said adaptive filter algorithm are estimated as one or more sinusoidal waves where the amplitude, the phase shift and the frequency are estimated by the adaptive filter algorithm.

3. System according to claim 2, wherein the one or more estimated noise components are estimated to be in the form $n = a \sin(\theta) + b \cos(\theta)$.

4. System according to claim 1, wherein the adaptive filter algorithm is based on a non-linear filter algorithm.

5. System according to claim 1, wherein said adaptive filter algorithm includes signals based on said one or more indifferent input signal(s).

6. System according to claim 1, wherein the system is further adapted to determine respective unipolar cardiac signals by subtracting one or more of the one or more indifferent signals from the cardiac signals and wherein the adaptive filter algorithm is run on one or more signals based on said unipolar cardiac signals.

7. System according to claim 1, wherein the system comprises one or more band pass filter(s) on the one or more cardiac signal(s), said band pass filter(s) being centered around the expected mains frequency or the expected harmonics of the mains frequency.

8. System according to claim 7, wherein the system compensates the one or more estimated noise components prior to subtracting it (them) from the input signal with the known phase shift of the band pass filter.

9. System according to claim 1, wherein the processor is adapted to analyse the frequency spectrum of one or more of the one or more cardiac signals or the one or more indifferent signals to determine the frequency or the frequencies which contribute(s) the most to the noise.

10. System according to claim 9, wherein the frequency analysis is performed via a Goertzel algorithm at the expected mains frequency and at harmonics of the expected mains frequency.

11. System according to claim 9, wherein the adaptive filter algorithm is run multiple times, starting with the frequency which has the greatest contribution to the noise, and repeated at harmonics thereof, an estimated sine wave of each frequency being subtracted from the input signal before running the algorithm for the next harmonic.

12. System according to claim 1, wherein the processor comprises a spike detection algorithm and wherein the processor stops the adaptive filter algorithm when a spike is detected in the cardiac signal.

13. System according to claim 1, wherein the adaptive filter algorithm is based on an extended Kalman filter or an unscented Kalman filter.

14. System for filtering cardiac signals, the system comprising:
a plurality of cardiac terminals adapted to collect cardiac electrophysiological potentials from a plurality of cardiac electrodes placed at respective cardiac locations in or on an individual;
an amplifier stage adapted to amplify the cardiac electrophysiological potentials collected from the cardiac terminals with respect to a signal reference to obtain a plurality of cardiac signals; and
a processor device adapted to process one or more input signals which are based on the cardiac signals,
wherein said processing comprises running an adaptive filter algorithm on one or more intermediate signals based on the input signals, said adaptive filter algorithm being arranged to calculate one or more estimated noise component(s) of said one or more intermediate signals and being arranged to subtract said one or more estimated noise component(s) respectively from said one or more intermediate signals;
wherein the processor is adapted to calculate an average of more than one signal based on the one or more cardiac signal(s), and
wherein said calculated average is used by the adaptive filter algorithm to provide a first estimate of the frequency of the noise component.

15. System according to claim 14, wherein the one or more estimated noise components of said adaptive filter algorithm are estimated as one or more sinusoidal waves where the amplitude, the phase shift and the frequency are estimated by the adaptive filter algorithm.

16. System according to claim 14, wherein the adaptive filter algorithm is based on a non-linear filter algorithm.

17. System according to claim 14, wherein the adaptive filter algorithm is based on an extended Kalman filter or an unscented Kalman filter.

18. System according to claim 14, wherein the system comprises one or more band pass filter(s) on the one or more cardiac signal(s), said band pass filter(s) being centered around the expected mains frequency or the expected harmonics of the mains frequency.

19. System according to claim 14, wherein the processor is adapted to analyze the frequency spectrum of one or more of the one or more cardiac signals to determine the frequency or the frequencies which contribute(s) the most to the noise.

20. System according to claim 14, wherein the processor comprises a spike detection algorithm and wherein the processor stops the adaptive filter algorithm when a spike is detected in the cardiac signal.

* * * * *